United States Patent [19]
Askin et al.

[11] Patent Number: 5,508,404
[45] Date of Patent: Apr. 16, 1996

[54] REDUCTIVE AMINATION PROCESS

[75] Inventors: David Askin, Warren, N.J.; Steven J. Cianciosi, Harrisonburg, Va.; Robert S. Hoerrner, Scotch Plains, N.J.

[73] Assignee: Merck & Co., Inc., Rahway, N.J.

[21] Appl. No.: 404,776

[22] Filed: Mar. 15, 1995

[51] Int. Cl.$^6$ .................................................. C07D 401/06
[52] U.S. Cl. ........................................................ 544/365
[58] Field of Search ................................................ 544/365

[56] References Cited

PUBLICATIONS

Abdel–Magid, et al., "Reductive Amination of Aldehydes and Ketones by Using Sodium Triacetoxyborohydride", Tet. Letters, vol. 31, No. 329, pp. 5595–5598, 1990.

Borch, et al., "The Cyanohydridoborate Anion as a Selective Reducing Agent", J. Am. Chem Soc., vol. 93.12, pp. 2897–2904, 1971.

March, "The Addition of Alcohols to Aldehydes and Ketones", Advanced Organic Chemistry (Third Edition), pp. 798–800, 1985.

*Primary Examiner*—John M. Ford
*Attorney, Agent, or Firm*—Roy D. Meredith; Jack L. Tribble

[57] ABSTRACT

A process of reductive amination efficiently yields an HIV protease inhibitor.

13 Claims, No Drawings

REDUCTIVE AMINATION PROCESS

BACKGROUND OF THE INVENTION

The present application is related to Merck 18996, U.S. Ser. No. 08/059,038, filed May 7, 1993 now abandoned.

The present invention is concerned with a novel intermediate and process for synthesizing compounds which inhibit the protease encoded by human immunodeficiency virus (HIV), and in particular certain oligopeptide analogs, such as compound J in the examples below. These compounds are of value in the prevention of infection by HIV, the treatment of infection by HIV and the treatment of the resulting acquired immune deficiency syndrome (AIDS). These compounds are also useful for inhibiting renin and other proteases.

The invention described herein concerns the final bond-forming step in the synthesis of the HIV protease inhibitor J. In the invention, the penultimate intermediate 1 is converted to J via introduction of a 3-picolyl moiety in the form of 3-pyridinecarboxaldehyde 2 via a reductive alkylation.

the HIV encoded protease resulted in the production of immature, non-infectious virus particles. These results indicate that inhibition of the HIV protease represents a viable method for the treatment of AIDS and the prevention or treatment of infection by HIV.

The nucleotide sequence of HIV shows the presence of a pol gene in one open reading frame [Ratner, L. et al., *Nature*, 313,277 (1985)]. Amino acid sequence homology provides evidence that the pol sequence encodes reverse transcriptase, an endonuclease and an HIV protease [Toh, H. et al., *EMBO J.*, 4, 1267 (1985); Power, M. D. et al., *Science*, 231, 1567 (1986); Pearl, L. H. et al., *Nature*, 329, 35 1 (1987)]. The end product compounds, including certain oligopeptide analogs that can be made from the novel intermediates and processes of this invention, are inhibitors of HIV protease, and are disclosed in EPO 541,168, which published on May 12, 1993. See, for example, compound J therein.

Previously, the synthesis of Compound J and related compounds was accomplished via a 12-step procedure. This procedure is described in EPO 541,168. The last step in prior

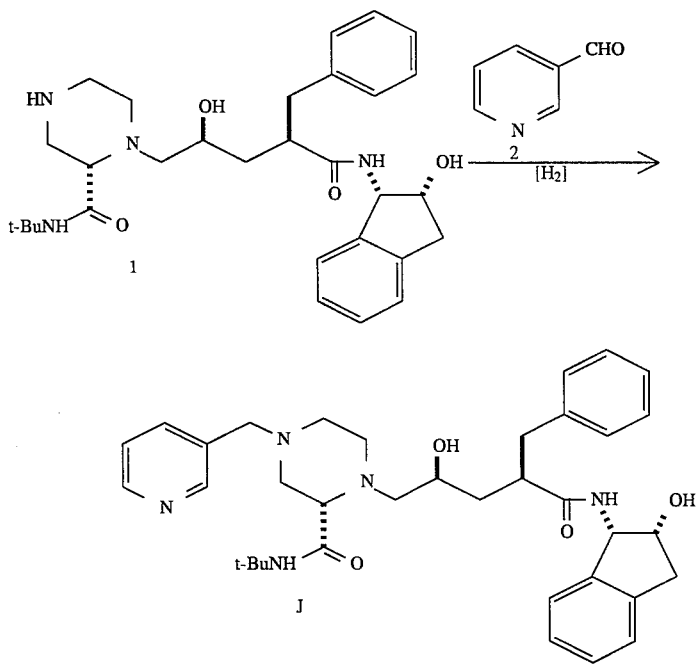

A retrovirus designated human immunodeficiency virus (HIV) is the etiological agent of the complex disease that includes progressive destruction of the immune system (acquired immune deficiency syndrome; AIDS) and degeneration of the central and peripheral nervous system. This virus was previously known as LAV, HTLV-III, or ARV. A common feature of retrovirus replication is the extensive post-translational processing of precursor polyproteins by a virally encoded protease to generate mature viral proteins required for virus assembly and function. Inhibition of this processing prevents the production of normally infectious virus. For example, Kohl, N. E. et al., *Proc. Nat'l Acad. Sci.*, 85, 4686 (1988) demonstrated that genetic inactivation of methods involved direct alkylation of the penultimate intermediate 1 with 3-picolyl chloride 3 to afford the HIV-protease inhibitor J. The disadvantage with this type of approach is the classical problem of overalkylation of amines with alkyl halides to form quaternary ammonium salts. In the present invention, overalkylation of the product J with 3-picolyl chloride, bromide or iodide results in the formation of the salt 4. Yield loss occurs. There are also difficulties in removing the salt 4, since multiple aqueous washes are required to effect complete removal. Complete removal of salt 4 by water washing is necessary.

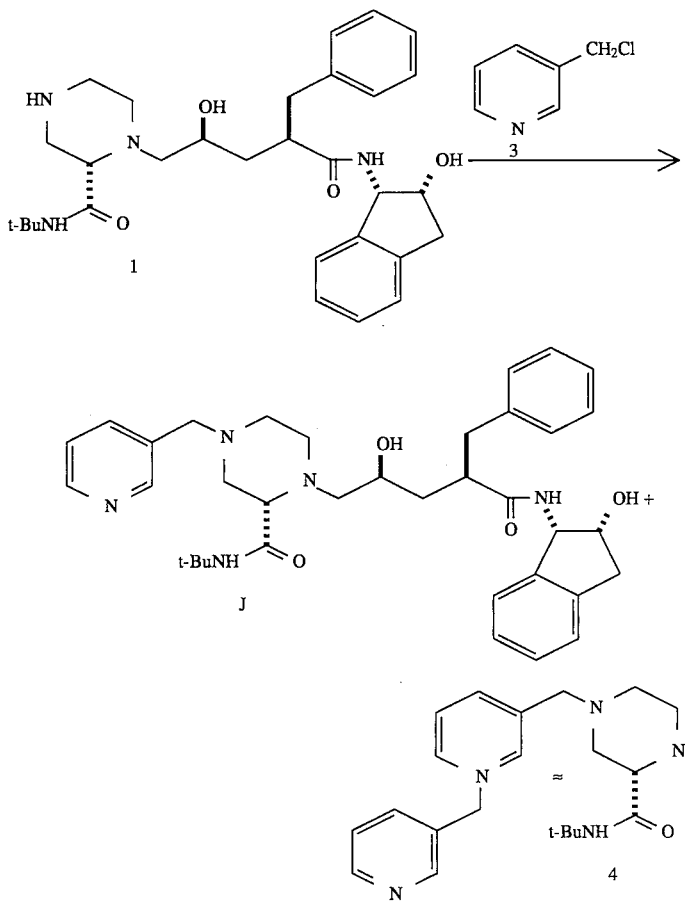

BRIEF DESCRIPTION OF THE INVENTION

The present invention provides new methods to effect synthesis of compounds by a reduction amination process.

The reductive alkylation of primary and secondary amines with carbonyl compounds is a classical reaction and is well documented in the literature [March, J. et al., in "Advanced Organic Chemistry", Third Edition, J. Wiley and Sons, New York, 1985, pp. 798–800]. The reductive alkylation of secondary amines by the use of aldehydes and NaCNBH$_3$ [Borch, R. F. et al., *J. Am. Chem. Soc.*, 1971, 93, 2897–2904] and NaH(OAc)$_3$ [Abdel-Mdgid, A. F. et al., *Tetrahedron Lett.*, 1990, 31, 5595–5598] has been reported more recently in the literature.

The advantage of the reductive amination in this invention is avoiding the formation of overalkylation byproducts. Thus, the isolation procedure is simplified with this alkylation procedure. The yield loss is also avoided.

The starting material 3-pyridinecarboxaldehyde 2 is also a more desirable intermediate for large scale processing. The starting material has a lower molecular weight than 3-picolyl chloride 3 (hydrochloride), and as such is more cost effective on a kilogram basis. It is a more stable and a more easily handled intermediate and is not carcinogenic or irritating as 3, and on a commercial basis it is substantially less expensive than 3. The unexpected finding was that the penultimate intermediate I could be converted to the product J in high yield and good purity by this method without complication of the other functionalities present in the starting material 1 or the product J. For example, condensation with the amino indanol end group was not found as a side reaction.

The product compound is useful as an inhibitor of HIV protease, renin and other proteases.

DETAILED DESCRIPTION OF THE INVENTION

The present invention provides new methods for making compound J of the structure

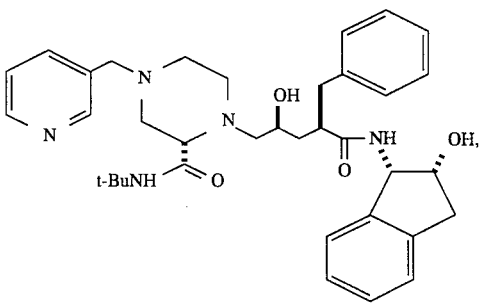

comprising the steps of:

(a) reacting for least 5 minutes in suitable solvent one equivalent of the compound having the structure

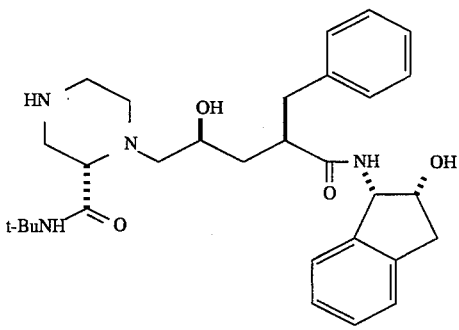

J with excess 3-pyridine carboxaldehyde in the presence of excess reducing agent, at a temperature range of between about –78° C. and about 90° C.;

(b) to give compound J or hydrate thereof.

Alternatively, the present invention provides a process for synthesizing compound J of the structure

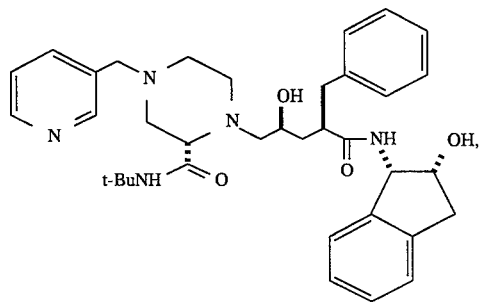

comprising the steps of:

(a) mixing in suitable solvent one equivalent of the compound having the structure

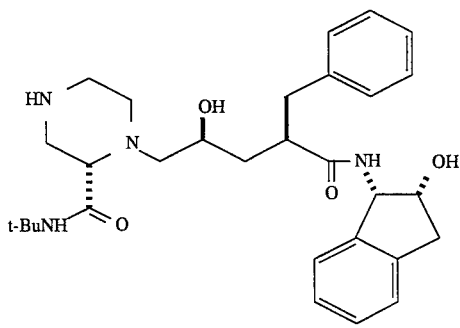

with excess 3-pyridine carboxaldehyde;

(b) adding excess reducing agent, and maintaining the resulting mixture for at least 5 minutes at a temperature range of between about –78° C. and about 90° C.;

(c) to give compound J or hydrate thereof.

In a preferred embodiment, this invention involves a process for synthesizing compound J of the structure

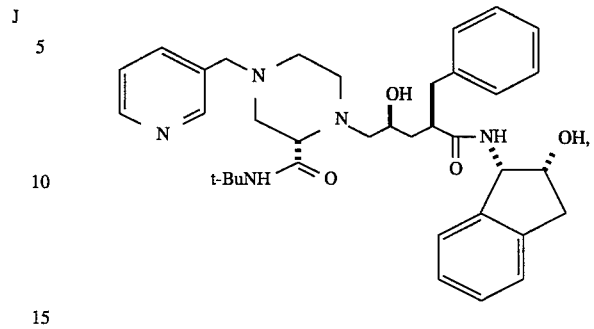

comprising the steps of:

(a) reacting for at least 5 minutes, in a solvent selected from isopropyl acetate and ethyl acetate, one equivalent of a compound having the structure

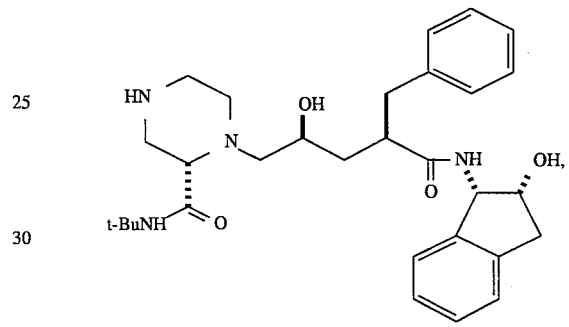

with between about one equivalent and about two equivalents of 3-pyridinecarboxaldehyde, in the presence of a reducing agent selected from NaBH(OAc)$_3$ and formic acid, at a temperature range between about 20° C. to about 60° C.;

(b) to provide compound J or hydrate thereof.

In another embodiment, this invention involves a process for synthesizing compound J of the structure

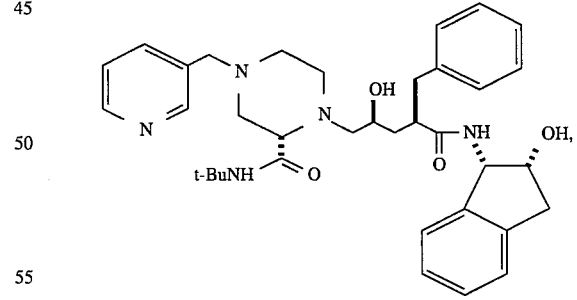

comprising the steps of:

(a) mixing in a solvent selected from isopropyl acetate and ethyl acetage, one equivalent of a compound having the structure

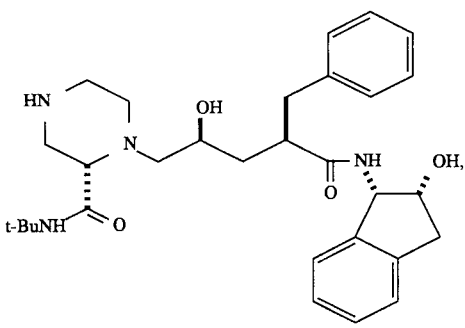

with between about one equivalent and about two equivalents of 3-pyridinecarboxaldehyde;

(b) adding a reducing agent selected from NaBH(OAc)₃ and formic acid, and maintaining the resulting mixture for at least 5 minutes at a temperature range between about 20° C. to about 60° C.;

(c) to provide compound J or hydrate thereof.

The process is amenable to a variety of solvents: esters such as ethyl acetate, isopropyl acetate; ethers such as diethyl ether, THF, DME; alcohols such as methanol, ethanol, isopropanol and aqueous alcohol systems; formamides such as DMF; hydrocarbon solvents such as cyclohexane and toluene; 1,2-dichloroethane. Preferred solvents include ester and alcohol solvents, and 1,2-dichloroethane. Most preferred solvents are esters such as isopropyl acetate and ethyl acetate. The process is carried out with a variety of reducing agents, such as heterogeneous catalytic hydrogenation agent, or reducing agents such as a NaBH₄, NaCNBH₃, NaBH(OAc)₃, Zn/HCl, Fe(CO)₅/KOH-EtOH, formic acid and selenophenol. Preferred reducing agents include NaCNBH₃, NaBH(OAc)₃ and formic acid. Most preferred reducing agents include NaBH(OAc)₃ and formic acid. The reductive alkylation is carried out at temperatures from −78° C. to 90° C. with a range of −40° C. to 70° C. more desirable and 20° C. to 60° C. most desired. Incubation times should be at least 5 minutes. Substantially complete reactions occur typically in 1–2 hours, and completeness is easily measured by conventional techniques.

The processes and intermediates of this invention are useful for the preparation of end-product compounds that are useful in the inhibition of HIV protease, the prevention or treatment of infection by the human immunodeficiency virus (HIV), and the treatment of consequent pathological conditions such as AIDS. Treating AIDS or preventing or treating infection by HIV is defined as including, but not limited to, treating a wide range of states of HIV infection: AIDS, ARC (AIDS related complex), both symptomatic and asymptomatic, and actual or potential exposure to HIV. For example, the end-product compounds that can be made from the processes and intermediates of this invention are useful in treating infection by HIV after suspected past exposure to HIV by, e.g., blood transfusion, organ transplant, exchange of body fluids, bites, accidental needle stick, or exposure to patient blood during surgery.

The end-product HIV protease inhibitors are also useful in the preparation and execution of screening assays for antiviral compounds. For example, end-product compounds are useful for isolating enzyme mutants, which are excellent screening tools for more powerful antiviral compounds. Furthermore, such compounds are useful in establishing or determining the binding site of other antivirals to HIV protease, e.g., by competitive inhibition. Thus the end-product compounds that are made from the processes and intermediates of this invention are commercial products to be sold for these purposes.

The end product HIV protease inhibitor compound J has the structure

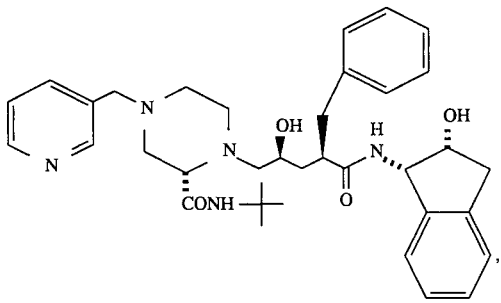

or pharmaceutically acceptable salts or hydrates thereof. Compound J is named

N-(2(R)-hydroxy-1(S)-indanyl)-2(R)-phenylmethyl-4(S)-hydroxy-5-(1-(4-(3-pyridylmethyl)-2(S)-N'-(t-butylcarboxamido)-piperazinyl))pentaneamide;

[1S-[1α[αS*,γR*,δ(R*)],2α]]-N-(2,3-dihydro-2-hydroxy-1H-inden-1-yl)-2[[(1,1-dimethylethyl)amino]carbonyl]-γ-hydroxy-α-(phenylmethyl)-4-(3-pyridinylmethyl)-1-piperazinepentaneamide; or N-(1(S)-2,3-dihydro-2(R)-hydroxy-1H-indenyl)-4(S)-hydroxy-2(R)-phenylmethyl-5-[4-(3-pyridylmethyl)-2(S)-(t-butylcarbamoyl)piperazinyl]pentaneamide.

HIV protease inhibitor compounds that can be made from the intermediates and processes of the instant invention are disclosed in EPO 541,164. The HIV protease inhibitory compounds may be administered to patients in need of such treatment in pharmaceutical compositions comprising a pharmaceutical carrier and therapeutically-effective amounts of the compound or a pharmaceutically acceptable salt thereof. EPO 541,164 discloses suitable pharmaceutical formulations, administration routes, salt forms and dosages for the compounds.

The compounds of the present invention, may have asymmetric centers and occur as racemates, racemic mixtures and as individual diastereomers, or enantiomers with all isomeric forms being included in the present invention. Also, combinations of solvents, substituents and/or variables are permissible only if such combinations result in stable compounds.

Representative experimental procedures utilizing the novel process are detailed below. These procedures are exemplary only and are not limitations on the novel process of this invention.

5,508,404

EXAMPLE 1

Experimental Procedure for Reductive Picolylation with NaH(OAc)₃

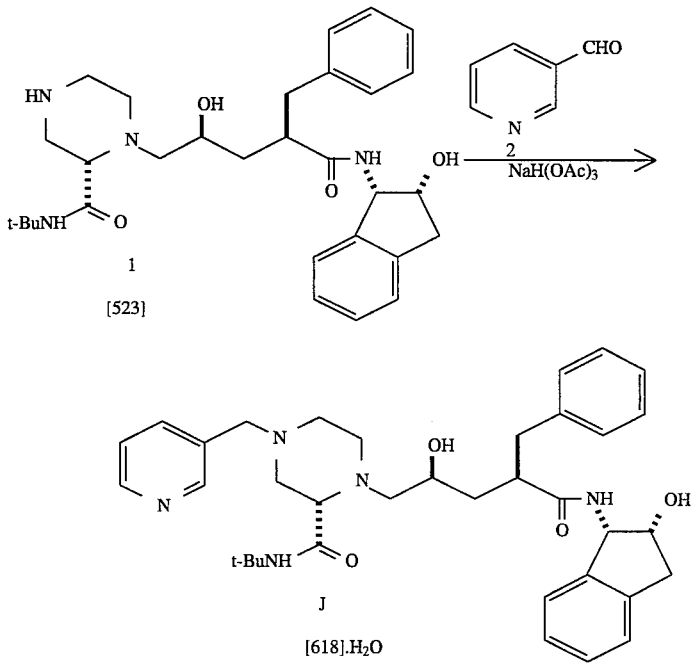

The penultimate intermediate 1 (1.00 g, 1.91 mmol) was dissolved in 20 mL of dry 1,2-dichloroethane and the aldehyde 2 (310 mg, 2.89 mmol) and sodium triacetoxyborohydride (600 mg, 2.83 mmol) were added. The resulting mixture was stirred at 21° C. After 1.25 h, the reaction was >99% complete. The reaction was quenched by adding 10 mL of saturated sodium bicarbonate, and the layers were separated. The organic layer was concentrated and the solvent was switched to isopropyl acetate. The crude mixture in 12 mL isopropyl acetate was heated to 85° C. and 300 mL of water was added to obtain a homogeneous solution with some second phase water present. The solution was slowly cooled to 5° C. and filtered and the crystals washed with (2×2 mL) isopropyl acetate. There was obtained 1.06 g of compound J as a monohydrate (88%) was a white crystalline solid that was >99.3 A% by HPLC analysis.

EXAMPLE 2

Experimental Procedure for Reductive Picolylation with Formic Acid

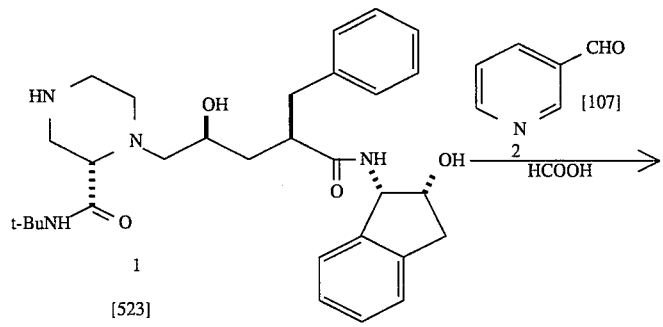

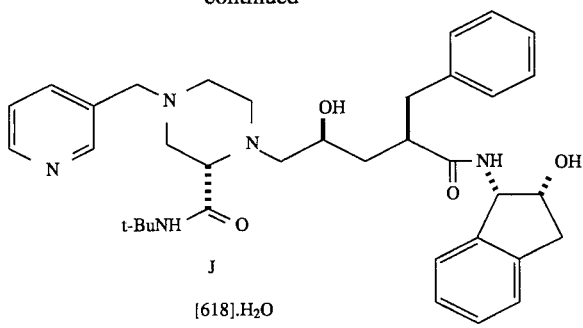

J

[618].H₂O

The penultimate intermediate 1 (2.5 g, 4.78 mmol) was suspended in 10 mL of isopropyl acetate at 20° C. and the aldehyde 2 (450 μL, 4.78 mmol) was charged and the slurry was warmed to 45°–50° C. to dissolve all the solids. Formic acid (200 μL, 5.3 mmol) was charged and mixture was aged at 50° C. for 2 h, at which time HPLC analysis indicated that the starting material 1 had been completely consumed. Aqueous NaOH (275 μL) was charged to adjust the pH to 7.0. The mixture was heated to 60°–65° C. and aged for 16 h, diluted with 25 mL of isopropyl acetate, washed at 65° C. with water, cooled to 25° C. and filtered. There was obtained 1.30 g (43%) of compound J as a white solid.

EXAMPLE 3

Conversion of Indene Oxide to Cis-1-Amino-2-Indanol

| Materials | Mol. Wt. | Grams or ml | Millimoles |
|---|---|---|---|
| Indene oxide | 132 | 1 ml | 8.33 |
| Acetonitrile | 41 | 10 ml | 244 |
| Water | 18 | 2.15 ml | 119.4 |
| Conc. H₂SO₄ | 98 | 0.92 ml | 16.6 |
| 5N KOH | 57 | 3.0 ml | 15 |
| Dowex 50 × 4 (H+) | 1.9 meq/ml | 15 ml wet resin | 28.5 meq |
| Methanol | 17 | 50 ml | 50 |

To one ml of indene oxide (8.33 moles) dissolved in 10 ml acetonitrile was added 0.15 ml water (8.33 mmoles). The mixture was cooled to 0°–5° in an ice bath. Concentrated sulfuric acid was added dropwise while maintaining the batch temperature below 10°. When all the acid was added and the temperature was allowed to rise to 20°–25°. The clear solution was aged for 30 minutes.

To this mixture was added 2 ml of water and the solution heated for 30 minutes. When the methyl oxazoline was completely converted to cis amino indanol the reaction mixture was cooled to room temperature.

A solution of 5N KOH (3 ml, 15 mmoles) was added. This is 90% of theory for the sulfuric acid. The solution remained acid to litmus. If the pH rises above, 2 re-acylation occurs and the yield of amino indanol is reduced. The white solid (K₂SO₄) was removed by filtration.

Dowex rosin 15 ml (wet with acetonitrile) was added with stirring. The stirred resin was aged for 15 minutes and sampled for LC (dilx 50). When the LC peak for amino indanol disappeared, the resin was collected by filtration, washed with acetonitrile and then with methanol.

The wet resin was treated with a solution of 50 ml 1N NH₃ in methanol and the slurry stirred at room temperature for 30 minutes. The resin was again collected by filtration and the methanol/NH₃ saved. Another charge of 1N NH₃/MeOH (20 ml) was added and the resin reslurried. After removal of the resin the methanol/NH₃ solutions of the amino indanol were combined and concentrated to remove the NH₃. Analysis of the final MeOH solution shows 1.0 g (81% yield)cis-1-amino-2-indanol ready for the tartaric acid resolving agent.

EXAMPLE 4

Preparation of racemic indene oxide

Indene (95%, 122 mL) was dissolved in methanol (812 mL) and acetonitrile (348 mL), then filtered. The filtrate was diluted with 0.05M sodium dibasic phosphate (116 mL), then adjusted to pH 10.5 with 1M aqueous sodium hydroxide. Aqueous hydrogen peroxide (35%, 105 mL) was diluted with water (53 mL) and added over 3 h, while maintaining the temperature at 25° C. and the internal pH at 10.5 with 1M aqueous sodium hydroxide (120 mL total).

After 6 h, 1M aqueous sodium metabisulfite was added (26 mL), while maintaining the pH above 8.3 by addition of 1 M aqueous NaOH (39 mL). Water (700 mL) was added and the mixture extracted with methylene chloride (580 mL and 300 mL). The combined organic extracts containing indene oxide (117 g) were concentrated to a volume of 600 mL.

EXAMPLE 5

Preparation of (1S, 2R)-indene oxide

The substrate, (1S, 2R)-indene oxide is prepared according to the method described by D. J. O'Donnell, et at., *J. Organic Chemistry*, 43, 4540 (1978), herein incorporated by reference for these purposes.

EXAMPLE 6

Preparation of cis-1-amino-2-indanol

Indene oxide (117 g) diluted to a total volume of 600 mL in methylene chloride was diluted with acetonitrile (600 mL) and cooled to −20° C. Methanesulfonic acid (114 mL) was then added. The mixture was warmed to 25° C. and aged for 2 h. Water (600 mL) was added and the mixture heated at 45° C. for 5 h. The organic phase was separated and the aqueous phase further heated at reflux for 4 h with concentration to approximately 200 g/L. The solution was adjusted to pH 12.5 with 50% aqueous sodium hydroxide, and then cooled to 5° C. and filtered, dried in vacuo, to provide cis 1-amino-2-indanol.

EXAMPLE 7

Preparation of 1S-amino-2R-indanol (1,S, 2R)-indene oxide (85% ee,) (250 g, 0.185 mole) was dissolved in chlorobenzene (300 mL) and heptanes (1200 mL) and slowly added to a solution of methanesulfonic acid (250 mL, 0.375 mole) in acetonitrile (1250 mL) at a temperature of less than about −10° C. The reaction mixture was warmed to 22° C. and aged for 1.0 h. Water was added to the mixture and concentrated by distillation until an internal temperature of 100° C. was achieved. The reaction mixture was heated at 100° C. for 2–3 h then cooled to room temperature. Chlorobenzene (1000 mL) was added, the mixture stirred, the organic phase separated. The remaining aqueous phase containing 1S-amino, 2R-indanol (85% ee, 165 g, 60%) was adjusted to pH 12 with 50% aqueous sodium hydroxide and the product collected by filtration and dried in vacuo at 40° C. to yield 1S-amino, 2R-indanol (85% ee, 160 g).

EXAMPLE 8

Preparation of 1S-amino-2R-indanol (1S, 2R)-indene oxide (85% ee,) (250 g, 0.185 mole) was dissolved in chlorobenzene (300 mL) and heptanes (1200 mL) and slowly added to a solution of fuming sulfuric acid (21% $SO_3$, 184 mL) in acetonitrile (1250 mL) at a temperature of less than about −10° C. The reaction mixture was warmed to 22° C. and aged for 1.0 h. Water was added to the mixture and concentrated by distillation until an internal temperature of 100° C. was achieved. The reaction mixture was heated at 100° C. for 2–3 h, then cooled to room temperature. Chlorobenzene (1000 mL) was added, the mixture stirred, the organic phase separated. The remaining aqueous phase containing 1S-amino, 2R-indanol (85% ee, 205 g, 74%) was diluted with an equal volume of acetonitrile. The pH was adjusted to 12.5 with 50% aqueous sodium hydroxide and the organic phase separated. The remaining aqueous phase was extracted with additional acetonitrile. The combined acetonitrile extracts were concentrated in vacuo to provide 1S-amino, 2R-indanol (85% ee, 205 g).

Alternatively, the remaining aqueous phase containing 1S-amino-2R-indanol (85% ee, 205 g, 74%) was diluted with an equal volume of butanol and the pH was adjusted to 12.5 with 50% aqueous sodium hydroxide and the organic phase separated. The organic phase was washed with chlorobenzene. L-tartaric acid was added and water was removed by distillation to crystallize the tartaric acid salt of the amino-indanol.

EXAMPLE 9

Use of benzonitrile

Indene oxide (5 g) was dissolved in benzonitrile (50 mL) at 25° C. and sulfuric acid (98%, 2.25 mL) was added. The mixture was diluted with 5M aqueous sodium hydroxide solution (50 mL) and extracted with methylene chloride. The organic extracts were concentrated in vacuo to give 5.03 g of oxazoline.

EXAMPLE 10

Resolution of cis-1-Amino-2-indanol

Cis-1-Amino-2-indanol (100 g) was dissolved in methanol (1500 mL) and a solution of L-tartaric acid (110 g) in methanol (1500 mL) was added. The mixture was heated to 60° C. and cooled to 20° C., filtered and dried in vacuo to give 1S-amino, 2R-indanol L-tartaric acid salt as a methanol solvate (88 g).

EXAMPLE 11

Preparation of 1S-Amino-2R-indanol

1S-Amino, 2R-indanol L-tartaric acid salt methanol solvate (88 g) was dissolved in water (180 mL) and heated to 55°–60° C. The solution was clarified by filtration and the pH adjusted to 12.5 with 50% aqueous sodium hydroxide. The mixture was cooled to 0°–5° C. over 2 h, then aged at that temperature for 1 h, filtered, washed with cold water and dried in vacuo at 40° C. to yield 1S-amino, 2R-indanol (100% ee, 99% pure, 37 g).

EXAMPLE 12

Conversion of 1,2 indanol to cis-1-amino-2-indanol

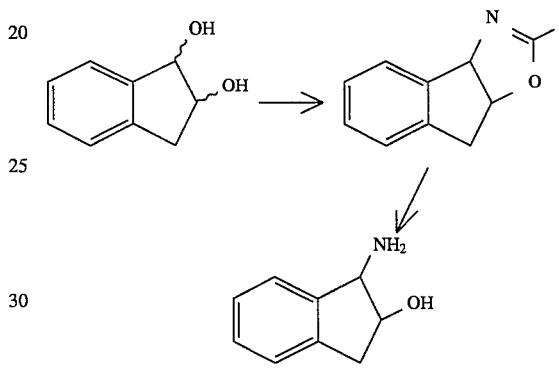

| Materials | Mol Wt | Grams or ml | Millimoles |
|---|---|---|---|
| 1,2 indane diol | 150 | 300 mg | 2 |
| acetonitrile | 41 | 2.5 ml | 47.3 |
| water | 18 | 0.04 ml | 2 |
| sulfuric acid | 98 | 0.22 ml | 4 |
| 5 N KOH | 57 | 1.6 ml | 8.0 |
| Dowex 50 × 4 (H+) | | 10 ml | |
| methanol (1 m $NH_3$) | | 30 ml | |

To 300 mg indane diol dissolved in 3 ml of acetonitrile containing 0.04 ml water was added dropwise at 0°–10° C. a volume of 0.22 ml of concentrated $H_2SO_4$. After the addition was complete the ice bath s was removed and the batch warmed to room temperature. After a 30 minute age the clear solution was sampled for Ic assay (dilx 500). When all the glycol was consumed, the solution was treated further with water and heated to reflux on a steam bath to hydrolyze the oxazoline.

When Ic analysis showed hydrolysis complete, 1.6 ml 5N KOH was added to neutralize the sulfuric acid. Potassium sulfate was filtered from the solution.

The filtrate was assayed for cis amino indanol and contained 196 mg (66% of theory, which is also 75% corrected for unreacted starting material). The solution was passed over 10 ml of Dowex 50×4 (H+). The column spents were checked for product. All the amino indanol was adsorbed. After washing the resin with methanol, the product was eluted with a solution 1M in $NH_3$ (dry). The ammoniacal methanol was concentrated to remove the $NH_3$ and the final solution of amino-indanol ready for resolution was assayed. (175 mg, or 59% of theory when uncorrected for unreacted glycol).

EXAMPLE 13

Preparation of Indanol Reactants

Compounds (±)-trans-2-bromo-1-indanol were prepared by methods of S. M. Sutter et at., *J. Am. Chem. Soc.*, 62, 3473 (1940); and D. R. Dalton et al., *J. C. S. Chem. Commun.*, 591 (1966). Compounds (+)-trans-2-bromo-1-indanol and cis- and trans-1,2-indandiols were prepared by the methods of M. Imuta et at., *J. Org. Chem.*, 43, 4540 (1978).

EXAMPLE 14

Preparation of cis-1-amino-2-indanol from trans-2-bromo-1-indanol

Trans-2-bromo-1-indanol (10 g, 46.9 mmole diluted in 100 mL of acetonitrile containing 0.8 mL water) was cooled to −5° C. and concentrated sulfuric acid (5.2 mL) was added. The mixture was aged for 1 h, then 5M aqueous potassium hydroxide was added to adjust the pH to 11. The reaction mixture was filtered, removing the potassium sulfate salts. The aqueous acetonitrile filtrate was adjusted to pH less than 2 with sulfuric acid and heated to 80°–100° C., removing acetonitrile by distillation to provide an aqueous solution of cis-1-amino-indanol. The solution was concentrated to a volume of 20 mL, then adjusted to pH 12.5 with potassium hydroxide. The product crystallizes, was filtered and dried in vacuo to provide cis-1-amino-2-indanol (4.25 g).

EXAMPLE 15

Preparation of cis-1S-amino-2R-indanol from cis-(1S,2R)-indandiol

Cis-(1S,2R)-indandiol (1 g) was dissolved in acetonitrile (10 mL), cooled to 0° C. and concentrated sulfuric acid (1.0 mL) was added. The mixture was aged for 40 minutes with warming to 20° C. Water (0.8 mL) was added and the mixture was heated to reflux. Aqueous 5M potassium hydroxide (1.6 mL) was added to adjust the pH to more than 11 and the resulting solid (potassium sulfate) removed by filtration to provide an aqueous solution of the cis-1S-amino-2R-indanol (0.79 g, 66% yield).

EXAMPLE 16

Preparation of cis-1-amino-2-indanol from trans-1,2-indandiol

Trans-1,2-indandiol (1.5 g) was dissolved in acetonitrile (25 mL) cooled to 0° C., and concentrated sulfuric acid (1.1 mL) was added. The mixture was gradually warmed to 20° C. and aged to 3 hours. Water (2 mL) was added and the mixture heated to reflux. Concentrated aqueous sodium hydroxide was added to adjust the pH to 12. The resulting solid was removed by filtration to provide an aqueous acetonitrile solution of cis-1-amino-2-indanol (1.02 g, 63% yield).

EXAMPLE 17

Preparation of cis-1-amino-2-indanol from cis-1,2-indandiol

Cis-1,2-indandiol (1.0 g) was dissolved in acetonitrile (20 mL), cooled to −40° C., and fuming sulfuric acid (21% $SO_3$, 0.8 mL) was added. The mixture was aged for 1 hour with gradual warming to 0° C. Water was added and the mixture heated to 80° C. for 1 hour to provide an aqueous solution of cis-1-amino-2-indanol.

EXAMPLE 18

Preparation of Amide 3

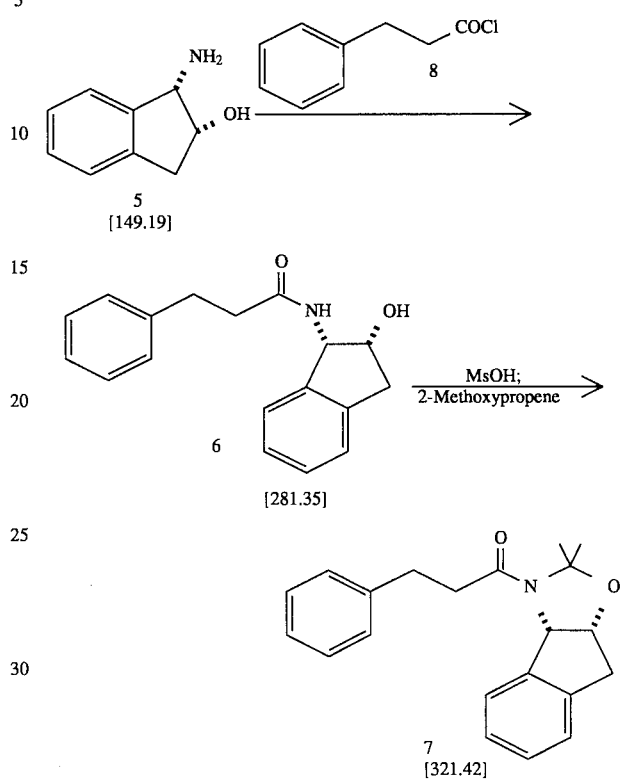

| | | |
|---|---|---|
| (−)-cis-1-aminoindan-2-ol (5) (99.7 wgt. %, 99.9 area %, >99.5% ee) | 900 g | 6.02 mol |
| sodium carbonate monohydrate | 760 g | 6.13 mol |
| diethoxymethane (DEM) | 56.3 L | |
| 3-phenylpropionyl chloride (8) | 1.05 kg | 6.23 mol |
| methanesulfonic acid (MSA) | 18.6 g | 0.19 mol |
| 2-methoxypropene (95% by GC) | 1.28 L | 13.3 mol |
| 5% aqueous $NaHCO_3$ | 10.8 L | |
| water | 26.2 L | |

A slurry mixture consisting of (−)-cis-1-aminoindan-2-ol (5, 900 g, 6.02 mol) in 40 L of DEM and aqueous sodium carbonate solution (760 g, 6.13 mol, of $Na_2CO_3 \cdot H_2O$ in 6.4 L of water) in a 100 L reactor with four inlets, equipped with a thermocouple probe, mechanical stirrer, and a nitrogen inlet adapter and bubbler, was heated to 46°–47° C. and aged for 15 minutes. The reaction mixture was heated to 46°–47° C. and aged for 15 minutes to insure dissolution of the solids. The aqueous phase had a pH of 11.5. Neat 3-phenylpropionyl chloride 8 (1.05 kg, 6.23 mol) was added over 2 h between 47° C. to 59° C. The internal temperature increased from 47° C. to 59° C. during the addition of 8; the hydroxyamide 6 crystallized out of solution during the acid chloride addition. After the addition was complete, the reaction mixture was aged at 59° C. for 0.5 h and then warmed to 72° C. to insure dissolution of the solids. The temperature was increased to 72° C. to dissolve the hydroxyamide so that a homogeneous sample can be obtained for HPLC assay and to simplify the phase cuts. Progress of the reaction was monitored by HPLC analysis: 60:40 Acetonitrile/5.0 mM of each $KH_2PO_4$ and $K_2HPO_4$. Approximate retention times:

| retention time (min.) | identity |
| --- | --- |
| 4.1 | hydroxy amide 6 |
| 6.3 | cis-aminoindanol 5 |
| 12.5 | ester amide by product |

After complete acid chloride addition and 0.5 h age at 72° C., the HPLC assay of the reaction mixture showed ~0.6 area % of 5, ~0.2 area % of ester amide by product and 98.7 area % of hydroxyamide. The hydroxy amide 6 was not efficiently rejected in the isolation of acetonide 7. The aqueous phase was separated and the organic phase was washed twice with 4.5 L of water. The washed organic phase was concentrated and dried via atmospheric azeotropic distillation. The initial volume of ~40 L was concentrated to 27 L. A total of 16 L of fresh DEM was charged to the still and the batch was concentrated at 88° C. to 89° C. to 40 L.

The dried DEM slurry of hydroxyamide 6 was treated with 1.28 L of 2-methoxypropene followed by 18.6 g of MSA at 30° C. The addition of MSA in absence of 2-methoxypropene resulted in the formation of an amine ester. This impurity reconverts to hydroxyamide 6 during the basic work up at the end of the acetonide formation. The pH of 1.0 mL sample diluted with 1.0 mL water was found to be 2.8–3.0. The resulting mixture was aged at 39° C. to 40° C. for 3 h. The acetonide formation was monitored by HPLC analysis using the same conditions as described above in this example. Approximate retention times:

| retention time (min.) | identity |
| --- | --- |
| 4.1 | hydroxy amide 6 |
| 6.9 | methylene ketal impurity |
| 9.0 | acetonide 7 |
| 12.5 | ester amide by product |

The mixture was aged at 38°–40° C. until 6 is ≦0.4 A %. A typical HPLC area % profile is as follows: 0.4 area % of hydroxyamide 6, 96.9 area % of acetonide 7, 0.2 area % of ester amide by product, 1.1 area % of methylene ketal impurity. The reaction mixture was cooled to 24° C. and quenched with 10.8 L of 5% aqueous sodium bicarbonate solution. The aqueous phase was separated and the organic phase was washed twice with 10.8 L of water. The pH of the water wash was 7.6. If the pH was too low, the acetonide group could be hydrolyzed back to give the hydroxyamide 6. The washed organic phase (34.2 L) was concentrated via atmospheric distillation at 78° C. to 80° C. to final volume of 3.5 L. The acetonide concentration was made ~525 g/L to minimize isolation losses. The hot DEM solution of 7 was allowed to cool to 57° C., seeded with 0.5 g of 7 and further cooled to 0° C. and aged for 0.5 h. The batch started to crystallize out of solution between 53° C. to 55° C. The product was isolated by filtration and the wet cake was washed with cold (0° C.) DEM (300 mL). The washed cake was dried under vacuum (26" of Hg) at 30° C. to afford 1.74 kg of acetonide 7 (90 %, >99.5 area % by HPLC).

EXAMPLE 19

Preparation of Acetonide 7 from (5• tartaric acid) salt

| | | |
| --- | --- | --- |
| (−)-cis-1-aminoindan-2-ol tartrate salt methanol solvate (44.3 wt. % of free base 5) | 100 g | 297 mmol |
| sodium carbonate monohydrate | 63.76 g | 514 mmol |
| diethoxymethane (DEM) | 2.83 L | |
| 3-phenylpropionyl chloride (8) | 52.7 g | 312 mol |
| methanesulfonic acid (MSA) | 0.95 g | 9.86 mmol |
| 2-methoxypropene (95% by GC) | 63 mL | 658 mmol |
| 5% aqueous NaHCO₃ | 520 mL | |
| water | 1.32 L | |

A slurry mixture consisting of (−) 5.tartrate salt methanol solvate (100 g, 44.3 g of free base, 297 mmol) in 2.0 L of (DEM) and aqueous sodium carbonate solution (63.8 g, 514 mmol, of Na₂CO₃•H₂O in 316 mL of water) in a 5.0 L reactor with four inlets, equipped with a thermocouple probe, mechanical stirrer, and a nitrogen inlet adapter and bubbler, was heated to 50° C. Heating the reaction mixture to 60° C. did not dissolve all the solids. Neat 3-phenylpropionyl chloride 8 (52.7 g, 312 mmol) was added over 30 min at 50° C. and the mixture was aged at 50° C. for 15 min. Progress of the reaction is monitored by HPLC analysis: 60:40 Acetonitrile/5.0 mM of each KH₂PO₄ and K₂HPO₄, 1.0 mL/min. Approximate retention times:

| retention time (min.) | identity |
| --- | --- |
| 4.1 | hydroxy amide 6 |
| 6.3 | cis-aminoindanol 5 |
| 12.5 | ester amide by product |

After complete acid chloride addition and 15 min. age at 50° C., the HPLC assay of the slurry mixture showed ~0.1 area % of 5. After this point, the reaction mixture was heated to 75° C.

The temperature was increased to 75° C. to dissolve the hydroxyamide 6 in DEM and simplify the phase separations. The aqueous phase was separated and the organic phase was washed twice with water (250 mL). The sodium tartrate was removed in the aqueous phase. The first aqueous cut had a pH of 8.98. The pH of the two water washes were 9.1 and 8.1, respectively. The washed organic phase was concentrated and dried via atmospheric distillation. Approximately 1.0 L of distillate was collected and 750 mL of fresh DEM was charged back to the distillation pot. The atmospheric distillation was continued until another 350 mL of distillate was collected. The solution KF was 93 mg/L. The dried DEM solution was cooled to 30° C. and treated with 63 mL of 2-methoxypropene followed by 0.95 g of MSA. The pH of 1.0 mL sample diluted with 1.0 mL water is 3.2. The reaction mixture was aged at 35°–42° C. for 2 h. The acetonide formation was monitored by HPLC analysis using the same conditions as described above in this Example. Approximate retention times: same as above. The mixture is aged at 38°–40° C. until 6 is ≦0.7 A%. A typical HPLC area % profile is as follows: 0.4 area % of hydroxy amide, 96.9 area % of acetonide 7, 0.2 area % of ester amide by product, 1.1 area % of methylene ketal impurity. The reaction mixture was cooled to 20° C., filtered to remove the cloudy appearance and quenched with 520 mL of 5% aqueous sodium bicarbonate solution. The aqueous phase was separated and the organic phase was washed with 500 mL of water. The pH of the water wash is 7.4. The washed organic phase (~2.0 L) was concentrated via atmospheric distillation at 78° C. to 80° C. to final volume of 1.0 L. The acetonide concentration in the isolation was maintained at ~525 g/L to minimize isolation losses. The hot DEM solution of 7 was allowed to cool to 50°–52° C., seeded with 100 mg of product and further cooled to 5° C. and aged for 20 min. The batch started to crystallize out of solution at 50° C. The product was isolated by filtration and the wet cake was washed with cold (0° C.) DEM (2×40 mL). The washed cake was dried under vacuum (26" of Hg) at 30° C. to afford 83.8 g of acetonide 7 (87.9 % >99.5 area % by HPLC).

EXAMPLE 20

Preparation of Acetonide 7 (Isopropyl Acetate Solvent)

| | | |
|---|---|---|
| (−)-cis-1-aminoindan-2-ol (5) (98.5 wgt. %) | 80 g | 535 mmol |
| isopropyl acetate (IPAC) | 1.2 L | |
| water | 560 mL | |
| 5N sodium hydroxide | 116 mL | 580 mmol |
| 3-phenylpropionyl chloride (8) | 90.8 g | 539 mmol |
| methanesulfonic acid (MSA) | 1.1 mL | 17.0 mmol |
| 2-methoxypropene (95% by GC) | 119 mL | 1.24 mol |
| 5% aqueous NaHCO$_3$ | 950 mL | |
| water | 400 mL | |
| methyl cyclohexane | 2.25 L | |

A mixture of (−)-cis-1-aminoindan-2-ol 5 (80 g, 535 mmol) in 1.2 L of IPAC and 560 mL of water was treated with 8 (90.8 g, 539 mmol) while the pH was maintained between 8.0–10.5 at 70°–72° C. with 5N sodium hydroxide (116 mL, 580 mmol).

Progress of the reaction was monitored by HPLC analysis: 60:40 Acetonitrile/5.0 mM of each KH$_2$PO$_4$ and K$_2$HPO$_4$. Approximate retention times:

| retention time min. | identity |
|---|---|
| 4.1 | hydroxy amide 6 |
| 6.3 | cis-aminoindanol 5 |
| 12.5 | ester amide by product |

At the end of the reaction, the aqueous phase was separated and the organic phase was washed with water (400 mL) at 72° C. –73° C. The pH of the aqueous phase and the aqueous wash was 8.1 and 7.9, respectively. The wet IPAC phase was dried via atmospheric distillation. A total of 3.0 L of IPAc was charged to lower the batch KF to <100 mg/L. The final volume is ~1.60 L. The resulting IPAC slurry of hydroxyamide 6 was treated with 2-methoxypropene (119 mL, 1.24 mol) followed by MSA (1.1 mL, 3.2 mole %) at 35° C. –38° C. for 4.5 h. The acetonide formation was monitored by HPLC analysis using the same conditions as described above. The mixture was aged at 38°–40° C. until 6 is <0.4 area %. The reaction was filtered to remove the hazy precipitate and the filtrate was quenched into cold sodium bicarbonate solution (950 mL) over 15 min. The aqueous phase was separated and the organic phase was washed with water (400 mL). The sodium bicarbonate solution was cooled to 0° C.–5° C. The pH of the aqueous phase and the aqueous wash was found to be 7.5 and 7.9, respectively. Atmospheric distillation was carried out while the solvent was switched to methylcyclohexane from IPAC. The initial volume before atmospheric concentration was 1.65 L. A total of 1.5 L of methylcyclohexane was added to complete the solvent switch to methylcyclohexane from IPAC. The batch temperature at the end of the solvent switch was 101° C. and the final batch volume was ~900 mL. The batch was heated to 65° C.–70° C. to insure dissolution of the solids, then cooled to 55° C., seeded with the product and cooled to 0° C. The mixture was aged at 0° C. for 15 min and the product was isolated by filtration and washed with cold methylcyclohexane (200 ml). The washed cake was dried under vacuum (26" of Hg) at 30° C. to afford 151 g of acetonide 7 (87.5 %, >99.5 area % by HPLC).

EXAMPLE 21

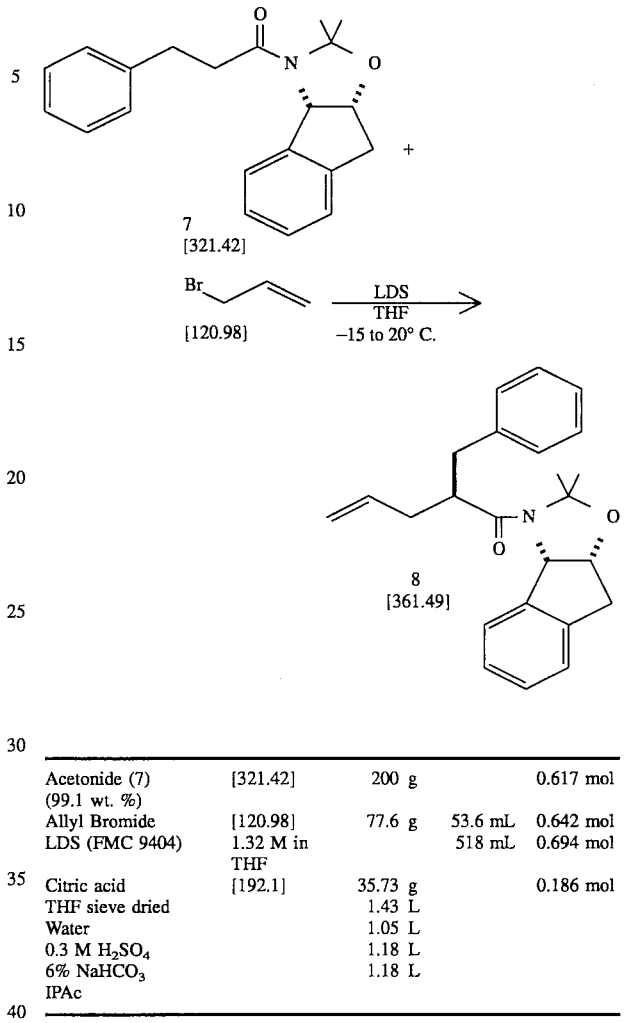

| | | | | |
|---|---|---|---|---|
| Acetonide (7) (99.1 wt. %) | [321.42] | 200 g | | 0.617 mol |
| Allyl Bromide | [120.98] | 77.6 g | 53.6 mL | 0.642 mol |
| LDS (FMC 9404) | 1.32 M in THF | | 518 mL | 0.694 mol |
| Citric acid | [192.1] | 35.73 g | | 0.186 mol |
| THF sieve dried | | 1.43 L | | |
| Water | | 1.05 L | | |
| 0.3 M H$_2$SO$_4$ | | 1.18 L | | |
| 6% NaHCO$_3$ | | 1.18 L | | |
| IPAc | | | | |

The crystalline acetonide 7 (200 g, 0.622 mol, 99.1 wt. %) was dissolved in 1.25 L sieve dried THF (KF=11 mg/L) under nitrogen atmosphere at 25° C. with mechanical stirring. The resulting KF of the solution at this point was 40 mg/L. The solution was subjected to three alternating vacuum/nitrogen purge cycles to thoroughly degas the solution of dissolved oxygen.

Allyl bromide was added to the THF solution. The resulting KF was 75 mg/L. Typical complete conversion (>99.5 %) has been obtained with pre-LDS solution KF levels of 200 mg/L with the 10 % base excess present in this procedure. The solution was then cooled to −20° C. A THF solution of lithium hexamethyldisilazide (LDS, 1.32M) was added to the allyl bromide/7 solution at such a rate as to maintain the reaction temperature at −20° C. The LDS addition took 30 min. The mixture was aged at −15° to −20° C. and quenched when the conversion was 99%. Analysis of the reaction was carried out by HPLC. Approximate retention times: hydroxyacetonide by product=5.3 min, ethyl benzene=5.6 min, acetonide 7=6.6 min; allyl acetonide 8=11.8 min; epi-8=13.3 min. After 1 h, the reaction had gone to >99.5% conversion. The reaction was quenched by the addition of a solution of citric acid (35.7 g, 0.186 mol) in 186 mL of THF. The mixture was aged at 15° C. for 30 min following the citric acid addition. The mixture was concentrated at reduced pressure (about 28" Hg) to about 30% of the initial volume while maintaining a pot temperature of 11°–15° C. and collecting 900 mL of distillate in a dry ice-cooled trap. The solvent was then switched using a total of 2.7 L of isopropyl acetate (IPAc) while continuing the reduced pressure distillation. The solvent switch was stopped when <1 mole % THF remained by $^1$H NMR (see analytical report for GC method). The maximum temperature during the distillation should not exceed 35° C. The crude mixture in IPAc was washed with 1.05 L of distilled water, 1.18 L of 0.3M sulfuric acid, and 1.18 L of 6% aqueous sodium bicarbonate. The volume of the organic phase after the washes was 1.86 L.

The pH of the mixture after the three aqueous washes was 6.5, 1.3 and 8.5, respectively. HPLC analysis of the mixture at this point indicated 93–94% assay yield for 8. The ratio of the desired 8:epi-8 was 96:4 by HPLC (same conditions as above). GC analysis at this point indicated that the hexamethyldisilazane by-product had been completely removed in the workup.

EXAMPLE 22

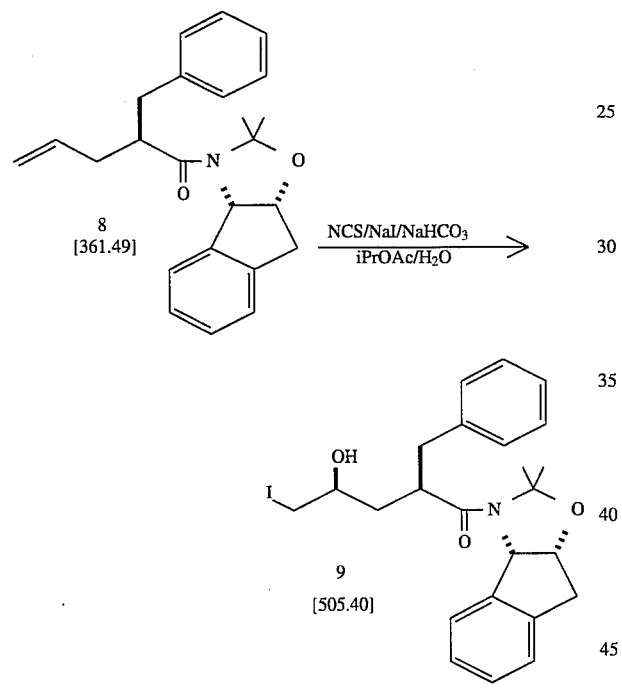

8
[361.49]

NCS/NaI/NaHCO$_3$
iPrOAc/H$_2$O

9
[505.40]

| | | | |
|---|---|---|---|
| NCS | [133.5] | 141.2 g | 1.06 mol |
| NaHCO$_3$ | [84.01] | 36.6 g | 0.434 mol |
| NaI | [149.9] | 158.6 g | 1.06 mol |
| Na$_2$SO$_3$ | [126.0] | 80 g | |
| Water | | 1.55 L | |

To the allyl amide 8 solution in IPAc from the previous step at 25° C. was added a solution of 36.6 g of sodium bicarbonate in 1.03 L of distilled water and the biphasic mixture was cooled to 5° C. Solid N-chlorosuccinimide (141.2 g, 1.06 mol) was added. There was no exotherm after the addition of NCS. To this mixture was added an aqueous solution of sodium iodide (158.6 g, 1.06 mol) while maintaining the reaction mixture at 6°–11° C. The addition took 30 min, and the mixture became dark. The mixture was warmed to 25° C. and aged with vigorous stirring. Progress of the reaction was monitored by HPLC: same system as above, approximate retention times: iodohydrins 9, epi-9, bis-epi-9=8.1 min; allyl amide 8=11.8 min. Analysis of the mixture by HPLC after 2.25 h indicated >99.5% conversion. The approximate diastereomer ratio of 9:epi-9:bis-epi-9 in the crude mixture is roughly 94:2:4 at this point when resolution of the components can be obtained on this system. The agitation was discontinued and the layers were separated. To the organic phase was added aqueous sodium sulfite (80 g, 0.635 mol in 400 mL) over 10–15 min. The temperature of the mixture rose from 26°–29° C. after the sodium sulfite addition. The mixture was agitated for 40 min at 25° C. The solution was substantially decolorized after the sulfite wash. The layers were separated; the KF of the organic phase at this point was 25 g/L. The volume of the organic phase was 1.97 L. Quantitative analysis of the mixture by HPLC (same system as above) indicated a 86% overall assay yield of the iodohydrin 9 at this point (corrected for coeluting diastereomers).

EXAMPLE 23

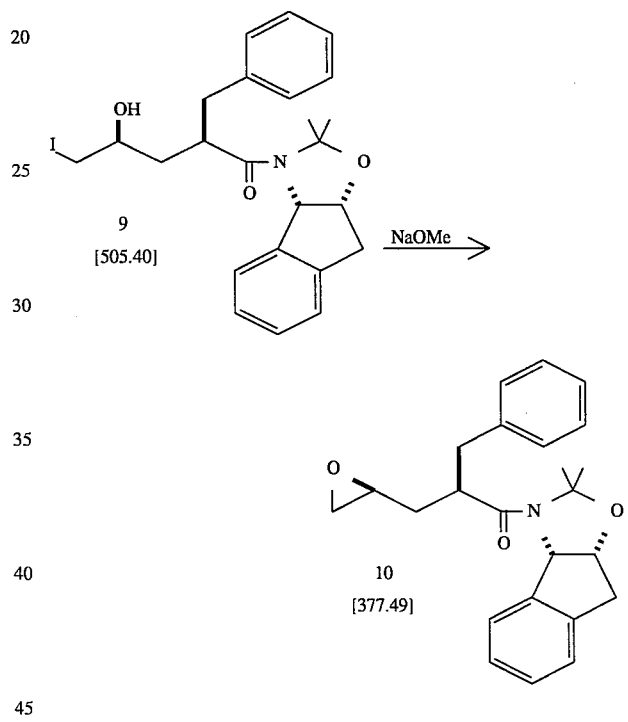

9
[505.40]

NaOMe

10
[377.49]

| | | | |
|---|---|---|---|
| NaOMe | [54.02] | d = 0.945 25 wt % in MeOH | 172 g |
| 0.796 mol | | | |
| 3% aqueous | | | 1.5 L |
| Na$_2$SO$_4$ | | | |
| n-PrOH | | | |

The solution of the iodohydrin 9 was concentrated in vacuo (28" Hg) to azeotropically dry the batch. A total of 700 mL of distillate was collected while maintaining a batch temperature of 22°–28° C. The distillate was replaced with 500 mL of IPAc (KF=275 mg/L).

The solution was cooled to 26° C. and 25% NaOMe/MeOH solution (168.1 g) was added over a 10 min period. The temperature dropped to 24° C. after the addition of sodium methoxide. The mixture became darker and a gummy solid briefly formed which redissolved. The mixture was aged for 1 h at 25° C. Analysis of the reaction was carried out by HPLC (same conditions as above), approximate retention times: epoxide epi-10=6.5 min, epoxide 10, bis-epi-10=7.1 min, iodohydrin 9=8.1 min. HPLC analysis indicated 99% conversion of the iodohydrin to the epoxide.

After an additional 40 rain, 4.1 g of the sodium methoxide/ methanol solution was added. After 20 min, HPLC analysis indicated 99.5% conversion. The reaction was quenched by the addition of 366 mL of water at 25° C. which was then agitated briefly (10 rain) and the layers were separated. It was subsequently found that extended aging of the reaction and water wash agitation/settling gave substantial back reaction to iodohydrin under these conditions in the pilot plant. This problem is especially acute in the water washes. To eliminate this problem, the reaction was run at 15° C. After >99% conversion was achieved (1 h after NaOMe addition), the mixture was diluted with IPAc (40% of batch volume) and initially washed with an increased volume of water (732 mL) at 20° C. Colder temperatures and more concentrated mixtures can result in the premature precipitation of 10 during the washes. The agitation/settling times were-kept to a minimum (10 min/30 min, respectively). In this way, the back reaction could be limited to ≦1 %. Crude mixtures containing (97:3) epoxide 10/iodohydrin 9 have been carried forward in the isolation to afford epoxide product containing 0.6 iodohydrin. Epoxide product containing this level of iodohydrin has been carried forward without complication. The organic phase was washed with 3% aqueous sodium sulfate (2×750 mL). The volume of the organic phase was 1.98 L after the washes. The pH of the three water washes was 10.7, 9.4 and 8.6, respectively. HPLC analysis indicated a 86% overall assay yield of epoxide 10 at this point (corrected for 4% co-eluting bis-epi-10). The IPAc solution of epoxide 10 was concentrated at reduced pressure (28" Hg) to a volume of about 600 mL while maintaining the batch at 15°–22° C. The solvent was switched to n-PrOH by adding 750 mL n-PrOH while vacuum concentrating to a pot volume of about 500 mL, maintaining the batch at <30° C. Temperatures >35° C. during the concentration/solvent switch can give an n-propyl ether as a degradation by-product derived from epoxide 10. Analysis of the solvent composition by $^1$H NMR showed <1 mol % IPAc remaining. The thick slurry was cooled to –10° C. over an hour and aged for 45 min. The solids were filtered and washed with 125 mL of cold nPrOH. The product was dried in a vacuum oven at 25° C. to afford 188.5 g of epoxide 10 (98.9 A %, 97.6 wt. %, 0.8 wt. % epi-10, 79.3% yield overall from 7.) Normal phase HPLC (see analytical research memo for procedure) indicated no bis-epi-10 present in the isolated solids.

EXAMPLE 24

Preparation of Penultimate 1

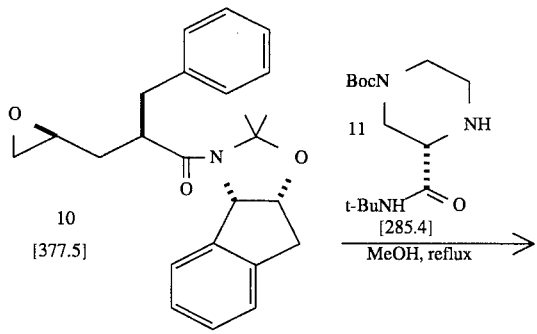

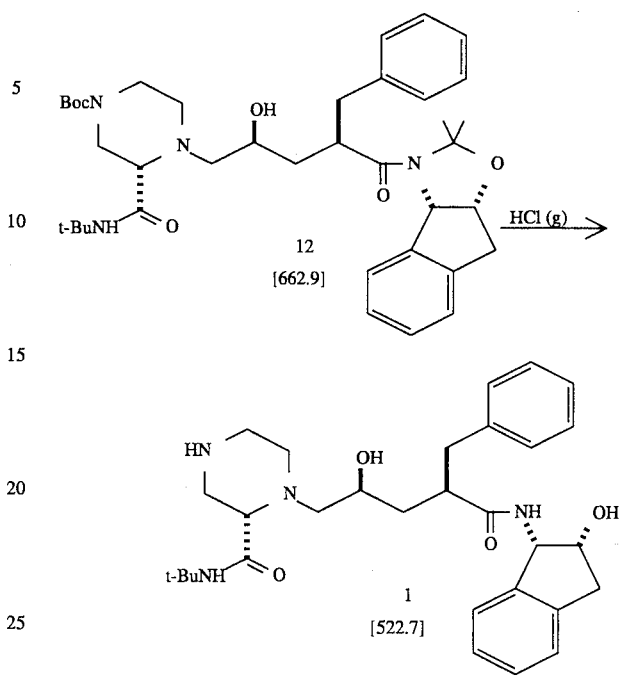

| | | |
|---|---|---|
| 2(S)-t-butylcarboxamide-4-N-Boc-piperazine 11 (98.9 wt. %, 99.6% ee) | 159 g | 557 mmol |
| epoxide 10 (97.6 wt. %, 1.0% epi-10) | 200 g | 530 mmol |
| methanol | 1.06 L | |
| HCl(g) | 194 g | 5.32 mol |
| 23% NaOH | 740 mL | |
| isopropyl acetate | 4.0 L | |
| water | 700 mL | |

*corrected for wt. % purity

Solid 2(S)-t-butylcarboxamide-4-t-butoxycarbonylpiperazine 11 (159 g, 557 mmol) and the epoxide 10 (200 g, 530 mol) were added to a 2 L three neck flask, equipped with a mechanical stirrer, reflux condenser, heating mantle, teflon coated thermocouple and nitrogen inlet. Methanol (756 mL) was added and the resulting slurry was heated to reflux temperature. After 40 min, a homogeneous solution was obtained. The internal temperature during reflux was 64°–65° C. Progress of the reaction was monitored by HPLC analysis: 60:40 acetonitrile/10 mM (KH$_2$PO$_4$/K$_2$HPO$_4$). Approximate retention times:

| retention time (min) | identity |
|---|---|
| 4.8 | piperazine 11 |
| 6.6 | methyl ether 13 |
| 8.2 | epoxide epi-10 |
| 8.9 | epoxide 10 |
| 15.2 | coupled product 12 |

The mixture was maintained at reflux until epoxide 10 was between 1.2 to 1.5 area % by HPLC analysis. The coupled product at this point was about 94–95 area %. The methyl ether 13 was present at 1.0–1.5 A % at completion. Typical time to achieve this conversion was 24–26 h at reflux.

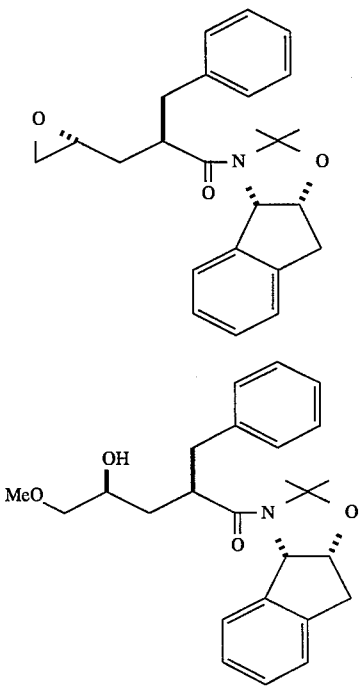

epi-10

13

The mixture was cooled to −5° C. and anhydrous HCl gas (194 g, 5.32 moles, ~10 equiv.) was bubbled directly into the methanol solution under nitrogen atmosphere while keeping the temperature between 5°–8° C. over 2–3 h. After the addition was complete, the mixture was aged between 5°–8° C. for 1–3 h. Evolution of gas was observed at this point (carbon dioxide and isobutylene). Progress of the reaction was monitored by HPLC analysis: same conditions as above. Approximate retention times:

| retention time (min) | identity |
|---|---|
| 6.0 | Boc intermediate 14 |
| 7.0 | cis-aminoindanol 15 |
| 11.9 | penultimate 1 |
| 15.1 | coupled product 12 |
| 16.5 | lactone 16 |
| 25.0 | acetonide intermediate 17 |

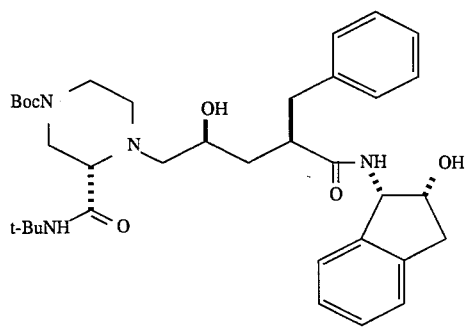

14

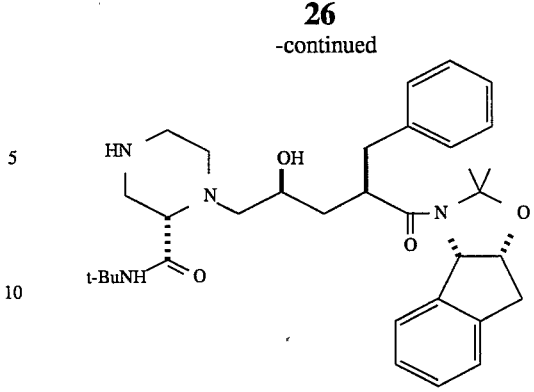

17

The mixture was aged at 5° to 8° C. until Boc intermediate 14 is <0.5 area % by HPLC analysis. At this point, penultimate 1 was about 92–93 A %, was <1.0 A % and 16 was 0.6 A % by HPLC analysis. The deblocking was complete after 4 h at 5° C. Cooling and quenching the reaction promptly upon completion limits decomposition of 1 to 15 and 16 under the hydrolysis conditions.

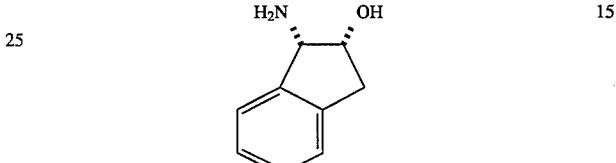

15

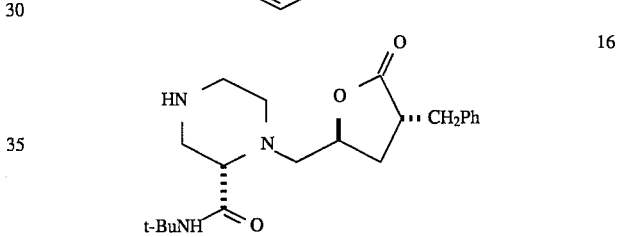

16

The mixture was cooled to −10° to −15° C. This mixture was then slowly added to a 5 liter flask equipped with a mechanical stirrer containing a cold, stirred solution of DI water (700 mL) and methanol (300 mL) at 0°–2° C.; the pH of the quenched mixture was maintained between 8.5–9.0 by addition of 23 wgt. % aqueous NaOH solution (giving a highly exothermic reaction) while keeping the temperature between 10–20° C. The final batch pH was 9.0–9.5.

The mixture was extracted with isopropyl acetate (3.0 L). The mixture was agitated and the layers were separated. The spent aqueous phase was re-extracted with isopropyl acetate (1.0 L). HPLC assay yield of 1 in isopropyl acetate at this point is 94%.

The combined organic phase (~5.0 L) was concentrated under reduced pressure (24–25" of Hg) to a volume of about 1.12 L at a batch temperature of 30°–40° C. The pot temperature during the solvent switch can rise to 40° C. with no penalty in yield or degradation. This solution of crude 1 was then used directly in the next step to afford compound J.

EXAMPLE 25

Preparation of monohydrate

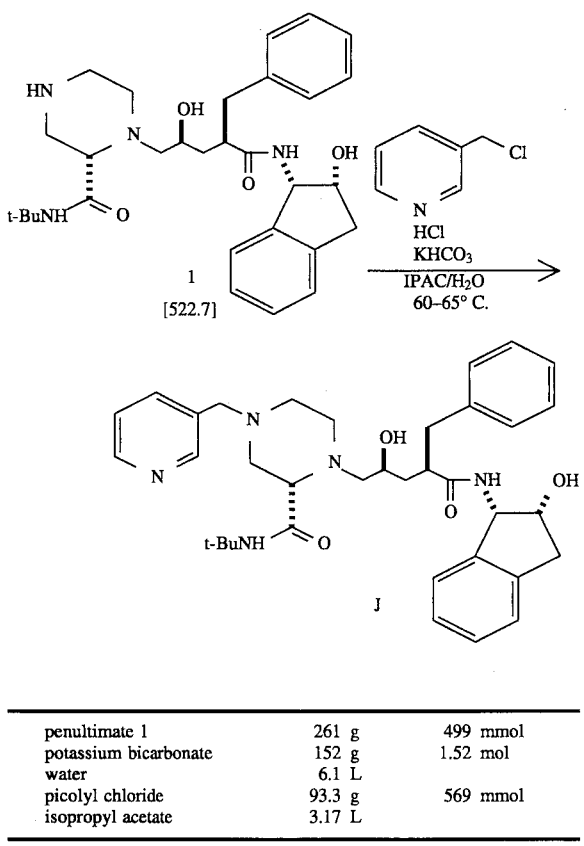

| penultimate 1 | 261 g | 499 mmol |
|---|---|---|
| potassium bicarbonate | 152 g | 1.52 mol |
| water | 6.1 L | |
| picolyl chloride | 93.3 g | 569 mmol |
| isopropyl acetate | 3.17 L | |

An isopropyl acetate solution of penultimate (4.96 L; 52.5 g/L of penultimate) was concentrated under reduced pressure to a volume of 1.18 L (260 g, 499 mmol). The batch temperature was maintained between 35° C. to 44° C. while keeping vacuum pressure at 25" of Hg. The methanol content was less than <1.0 vol %.

The resulting slurry was treated with an aqueous solution of potassium bicarbonate (152 g in 630 mL of water, 1.59 mol, ~3.0 equiv.) and heated to 60° C. Then, an aqueous solution of picolyl chloride (93.8 g in 94 mL of water; 572 mmol, 1.14 equiv.) was added over 4 hours. The batch was seeded with compound J monohydrate after charging 75% of the picolyl chloride charge. The batch temperature was between 60° C. to 65° C.

At the end of the addition, the slurry mixture was aged for 20 h between 60° C. to 65° C. The reaction was complete when the penultimate is <1.0 area % by HPLC analysis. The picolyl chloride level was between 0.5 to 0.8 area %.

The batch was then diluted with 2.5 L of isopropyl acetate and 1.34 L of water and heated to 78° C. The layers were separated and the organic phase was washed with hot water (3×1.34 L) at 78° C. The hot water wash removed the bis-alkylated compound J and the level was reduced to <0.1 area % by HPLC analysis.

The organic phase was slowly cooled to 75° C. and seeded with compound J monohydrate (8.0 g) and then further cooled to 4° C. over 2 h. The mixture was filtered to collect the product and the wet cake was washed with cold isopropyl acetate (2×335 mL). The wet cake was dried in vacuo (28" Hg, 22° C.) to afford 273 g of compound J monohydrate in 79% isolated yield from the epoxide.

EXAMPLE 26

Pyrazine-2-tert-butyl carboxamide 19

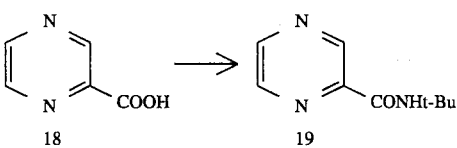

| 2-Pyrazinecarboxylic acid (18) | 3.35 kg (27 mol) |
|---|---|
| Oxalyl chloride | 3.46 kg (27.2 mol) |
| tert-Butylamine (KF = 460 µg/ml) | 9.36 L (89 mol) |
| EtOAc (KF = 56 µg/ml) | 27 L |
| DMF | 120 mL |
| 1-Propanol | 30 L |

The carboxylic acid 18 was suspended in 27 L of EtOAc and 120 mL of DMF in a 72 L 3-neck flask with mechanical stirring under $N_2$ and the suspension was cooled to 2° C. The oxalyl chloride was added, maintaining the temperature between 5 and 8° C.

The addition was completed in 5 h. During the exothermic addition CO and $CO_2$ were evolved. The HCl that was formed remained largely in solution. A precipitate was present which is probably the HCL salt of the pyrazine acid chloride. Assay of the acid chloride formation was carried out by quenching an anhydrous sample of the reaction with t-butylamine. At completion <0.7% of acid 18 remained.

The assay for completion of the acid chloride formation is important because incomplete reaction leads to formation of a bis-tert-butyl oxamide impurity.

The reaction can be monitored by HPLC:25 cm Dupont Zorbax RXC8 column with 1 mL/min flow and detection at 250 nm; linear gradient from 98% of 0.1% aqueous $H_3PO_4$ and 2% $CH_3CN$ to 50% aqueous $H_3PO_4$ and 50% $CH_3CN$ at 30 min. Retention times: acid 18=10.7 rain, amide 19=28.1 min.

The reaction mixture was aged at 5° C. for 1 h. The resulting slurry was cooled to 0° C. and the tert-butylamine was added at such a rate as to keep the internal temperature below 20° C.

The addition required 6 h, as the reaction was very exothermic. A small portion of the generated tert-butylammonium hydrochloride was swept out of the reaction as a fluffy white solid.

The mixture was aged at 18° C. for an additional 30 min. The precipitated ammonium salts were removed by filtration. The filter cake was washed with 12 L of EtOAc. The combined organic phases were washed with 6 L of a 3% $NaHCO_3$ and 2×2 L of saturated aq. NaCl. The organic phase was treated with 200 g of Darco G60 carbon and filtered through Solka Flok and the cake was washed with 4 L of EtOAc.

Carbon treatment efficiently removed some purple color in the product.

The EtOAc solution of 19 was concentrated at 10 mbar to 25% of the original volume. 30 L of 1-propanol were added, and the distillation was continued until a final volume of 20 L was reached.

At this point, the EtOAc was below the limit of detection in the $^1H$ NMR (<1%). The internal temperature in this solvent change was <30° C. A 1-propanol/EtOAC solution of 3 was stable to reflux at atmospheric pressure for several days.

Evaporation of an aliquot gave a tan solid m.p 87°–88° C. $^{13}$C NMR (75 MHz, CDCl$_3$, ppm) 161.8, 146.8, 145.0, 143.8, 142.1, 51.0, 28.5.

EXAMPLE 27 rac-2-tert-Butyl-carboxamide-piperazine 20

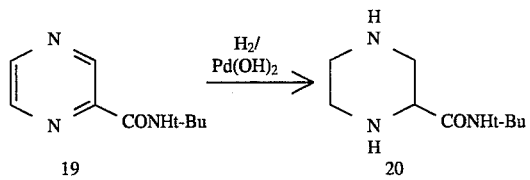

Materials

Pyrazine-2-tert-butylcarboxamide 19 2.4 kg (13.4 mol) in 1-Propanol solution 12 L 20% Pd(OH)$_2$/C 16 wt.% water 144 g The pyrazine-2-tert-butylcarboxamide 19/1-propanol solution was placed into the 5 gal autoclave. The catalyst was added and the mixture was hydrogenated at 65° C. at 40 psi (3 atm) of H$_2$.

After 24 h. the reaction had taken up the theoretical amount of hydrogen and GC indicated <1% of 19. The mixture was cooled, purged with N$_2$ and the catalyst was removed by filtration through Solka Floc. The catalyst was washed with 2 L of warm 1-propanol.

It was found that the use of warm 1-propanol during washing of the filter cake improved filtration and lowered the losses of product on the filter cake.

The reaction was monitored by GC:30 m Megabore column, from 100° C. to 160° C. at 10° C./min, hold 5 min, then at 10° C./min to 250° C., retention times: 19=7.0 min, 20=9.4 min. The reaction could also be monitored by TLC with EtOAc/MeOH (50:50) as solvent and Ninhydrin as developing agent.

Evaporation of an aliquot indicated that the yield over amidation and hydrogenation is 88% and that the concentration of 20 is 133g/L.

Evaporation of an aliquot gave 20 as a white solid m.p. 150°–151° C.; $^{13}$C NMR (75 MHz, D$_2$O, ppm) 173.5, 59.8, 52.0, 48.7, 45.0, 44.8, 28.7.

EXAMPLE 28

(S)-2-tert-Butyl-carboxamide-piperazine Bis (S)-Camphorsulfonic acid salt (S)-21

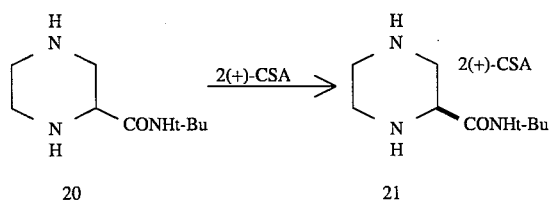

| Materials | |
|---|---|
| rac-2-tert-Butyl-carboxamide-piperazine 20 in 1-Propanol Solution | 4.10 kg (22.12 mol) in 25.5 Kg solvent |
| (S)-(+)-10-Camphorsulfonic acid | 10.0 Kg (43.2 mol) |
| 1-Propanol | 12 L |
| Acetonitrile | 39 L |
| Water | 2.4 L |

The solution of amine 20 in 1-propanol was charged to a 100 L flask with an attached batch concentrator. The solution was concentrated at 10 mbar and a temperature <25° C. to a volume of ca 12 L.

At this point the product had precipitated from the solution, but went back into a solution when the mixture was heated to 50° C.

Analysis of a homogeneous aliquot indicated that the concentration of 20 was 341 g/L The concentration was determined by HPLC: 25 cm Dupont Zorbax RXC8 column with 1.5 mL/min flow and detection at 210 nm, isocratic (98/2) CH$_3$CN/0.1% aqueous H$_3$PO$_4$. Retention time of 20:2.5 min.

Acetonitrile (39 L) and water (2.4 L) were added to give a clear, slightly brown solution.

Determination of the water content by KF titration and CH$_3$CN/1-propanol ratio by $^1$H NMR integration showed that the CH3CN/1-propanol/H$_2$O ratio was 26/8/1.6. The concentration in the solution was 72.2 g/L.

The (S)-10-camphorsulfonic acid was charged over 30 min in 4 portions at 20° C. The temperature rose to 40° C. after the CSA was added. After a few minutes a thick white precipitate formed. The white slurry was heated to 76° C. to dissolve all the solids, the slightly brown solution was then allowed to cool to 21° C. over 8 h.

The product precipitated at 62° C. The product was filtered without aging at 21° C., and the filter cake was washed with 5 L of the CH$_3$CN/1-propanol/H$_2$O 26/8/1.6 solvent mixture. It was dried at 35° C. in the vacuum oven with N$_2$ bleed to give 5.6 Kg (39%) of 21 as a white crystalline solid m.p 288°–290° C. (with decomp.) [α]$_D^{25}$= 18.9° (c=0.37, H$_2$O). $^{13}$C NMR (75 MHz, D$_2$O, ppm) 222.0, 164.0, 59.3, 54.9, 53.3, 49.0, 48.1, 43.6, 43.5, 43.1, 40.6, 40.4, 28.5, 27.2, 25.4, 19.9, 19.8.

The ee of the material was 95% according to the following chiral HPLC assay: an aliquot of 21 (33 mg) was suspended in 4 mL of EtOH and 1 mL of Et$_3$N. Boc$_2$O (11 mg) was added and the reaction mixture was allowed to age for 1 h. The solvent was completely removed in vacuo, and the residue was dissolved in ca. 1 mL of EtOAc and filtered through a Pasteur pipet with SiO$_2$, using EtOAc as eluent. The evaporated product fractions were redissolved in hexanes at ca. 1 mg/mL. The enantiomers were separated on a Daicel Chiracell AS column with a hexane/IPA (97:3) solvent system at a flow rate of 1 mL/min and detection at 228 nm. Retention times: S antipode=7.4 min, R=9.7 min.

EXAMPLE 29

(S)-2-tert-Butylcarboxamide-4-tert-butoxycarbonyl-piperazine 11 from salt 21

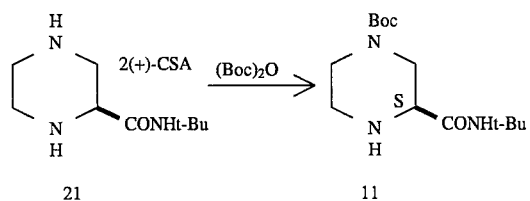

| Materials | |
|---|---|
| (S)-2-tert-Butyl-carboxamide-piperazine Bis (S)-(+)-CSA salt 21, 95% ee | 5.54 Kg (8.53 mol) |
| Di-tert-butyl dicarbonate | 1.86 Kg (8.53 mol) |
| Et$_3$N | 5.95 L (42.6 mol) |

| Materials | |
|---|---|
| EtOH Punctilious 200 proof | 55 L |
| EtOAc | 2 L |

To the (S)-CSA salt 21 in a 100 L 3-neck flask with an addition funnel under $N_2$ was added EtOH, followed by triethylamine at 25° C. The solid dissolved readily on the addition of the $Et_3N$. The $Boc_2O$ was dissolved in EtOAc and charged to the addition funnel. The solution of $Boc_2O$ in EtOAc was added at such a rate as to keep the temperature below 25° C. The addition took 3 h. The reaction mixture was aged for 1 h after completion of the addition of the $Boc_2O$ solution.

The reaction can be monitored by HPLC:25 cm Dupont Zorbax RXC8 column with 1 mL/min flow and detection at 228 nm, isocratic (50/50) $CH_3CN$/0.1M $KH_2PO_4$ adjusted to pH=6.8 with NaOH. Retention time of 11=7.2 min. The chiral assay was carried out using the same system as in the previous step. The reaction could also be monitored by TLC with a 100% EtOAc as the solvent. ($R_f$=0.7)

The solution was then concentrated to ca. 10 L at an internal temperature of <20° C. in a batch-type concentrator under 10 mbar vacuum. The solvent switch was completed by slowly bleeding in 20 L of EtOAc and reconcentrating to ca 10 L. The reaction mixture was washed into an extractor with 60 L of EtOAc. The organic phase was washed with 16 L of 5% aqueous $Na_2CO_3$ solution, 2×10 L Di water and 2×6 L of saturated aqueous sodium chloride. The combined aqueous washes were back extracted with 20 L of EtOAc and the organic phase was washed with 2×3 L water and 2×4 L of saturated aqueous sodium chloride. The combined EtOAc extracts were concentrated under 10 mbar vacuum with an internal temperature of <20° C. in a 100 L batch-type concentrator to ca. 8 L. The solvent switch to cyclohexane was achieved by slowly bleeding in ca. 20 L of cyclohexane, and reconcentrating to ca. 8 L. To the slurry was added 5 L of cyclohexane and 280 mL of EtOAc and the mixture was heated to reflux, when everything went into solution. The solution was cooled and seed (10 g) was added at 58° C. The slurry was cooled to 22° C. in 4 h and the product was isolated by filtration after a 1 h age at 22° C. The filter cake was washed with 1.8 L of cyclohexane and dried in the vacuum oven at 35° C. under $N_2$ bleed to give 1.87 Kg (77%, >99.9 area % by HPLC, R-isomer below level of detection) of 11 as a slightly tan powder. $[\alpha]D^{25}$=22.0° (c=0.20, MeOH), m.p 107° C.; $^{13}C$ NMR (75 MHz, $CDCl_3$, ppm) 170.1, 154.5, 79.8, 58.7, 50.6, 46.6, 43.6, 43.4, 28.6, 28.3.

While the foregoing specification teaches the principles of the present invention, with examples provided for the purpose of illustration, it will be understood that the practice of the invention encompasses all of the usual variations, adaptations, and modifications, as come within the scope of the following claims and its equivalents.

What is claimed is:

1. A process for synthesizing compound J of the structure

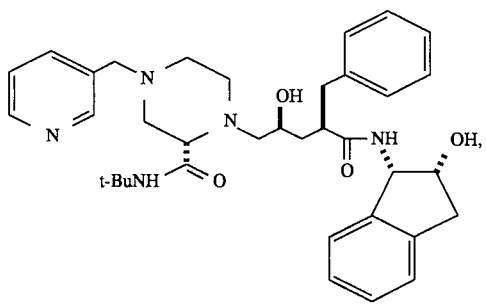

comprising the steps of:
(a) reacting for at least 5 minutes in suitable solvent one equivalent of the compound having the structure

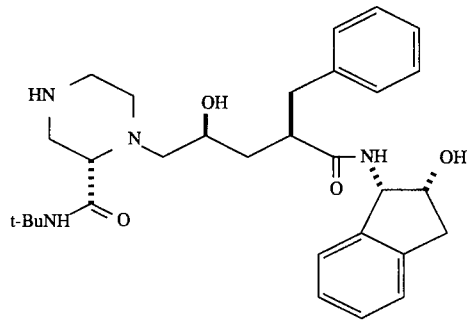

with excess 3-pyridine carboxaldehyde in the presence of excess reducing agent, at a temperature range of between about −78° C. and about 90° C.;
(b) to give compound J or hydrate thereof.

2. A process for synthesizing compound J of the structure

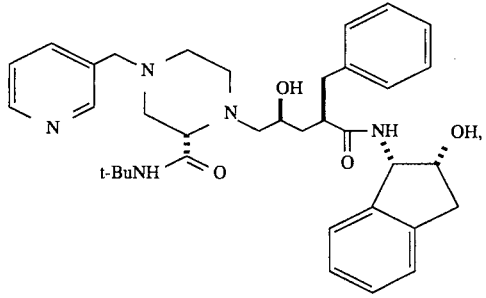

comprising the steps of:
(a) mixing in suitable solvent one equivalent of the compound having the structure

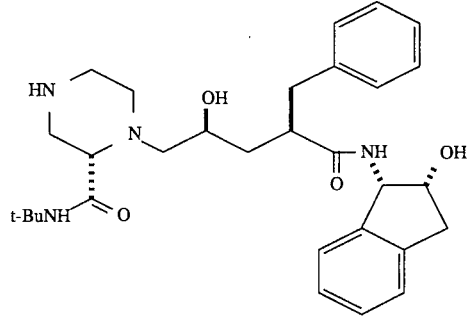

with excess 3-pyridine carboxaldehyde;

(b) adding excess reducing agent, and maintaining the resulting mixture for at least 5 minutes at a temperature range of between about −78° C. and about 90° C.;

(c) to give compound J or hydrate thereof.

3. The process of claim 1 or 2, wherein the suitable solvent is selected from an ester, an ether, an alcohol, a formamide, a hydrocarbon, and 1,2-dichloroethane, and any mixture of these solvents.

4. The process of claim 1 or 2, wherein the suitable solvent is selected from an ester and an alcohol or both.

5. The process of claim 1 or 2 wherein the suitable solvent is selected from isopropyl acetate and ethyl acetate.

6. The process of claim 1 or 2 wherein the reducing agent comprises a catalytic hydrogenation agent.

7. The process of claim 1 or 2 wherein the reducing agent comprises a reducing agent selected from $NaBH_4$, $NaCNBH_3$, $NaBH(OAc)_3$, $Zn/HCl$, $Fe(CO)_5/KOH$-EtOH, formic acid and selenophenol.

8. The process of claim 6 wherein the reducing agent comprises a reducing agent selected from $NaCNBH_3$, $NaBH(OAc)_3$ and formic acid.

9. The process of claim 7, wherein the reducing agent comprises a reducing agent selected from $NaBH(OAc)_3$ and formic acid.

10. The process of claim 1 or 2, wherein the temperature range of the reaction of Step (a) in claim 1 or of Step (b) in claim 2 is carried out between about −40° C. and about 70° C.

11. The process of claim 9, wherein the temperature range of the reaction of Step (a) in claim 1 or of Step (b) in claim 2 is carried out between about 20° C. and about 60° C.

12. A process for synthesizing compound J of the structure

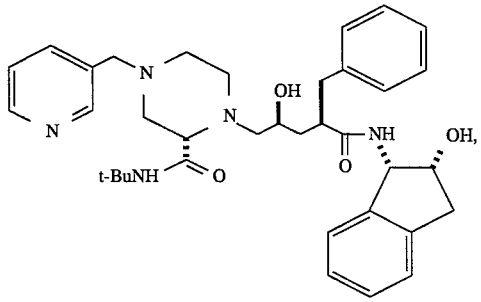

comprising the steps of:

(a) reacting for at least 5 minutes, in a solvent selected from isopropyl acetate and ethyl acetate, one equivalent of a compound having the structure

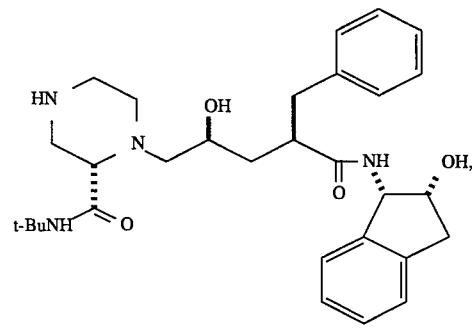

with between about one equivalent and about two equivalents of 3-pyridinecarboxaldehyde, in the presence of a reducing agent selected from $NaBH(OAc)_3$ and formic acid, at a temperature range between about 20° C. to about 60° C.;

(b) to provide compound J or hydrate thereof.

13. A process for synthesizing compound J of the structure

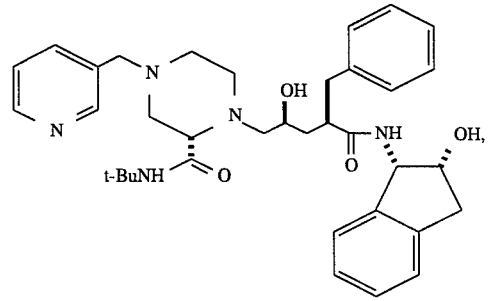

comprising the steps of:

(a) mixing in a solvent selected from isopropyl acetate and ethyl acetage, one equivalent of a compound having the structure

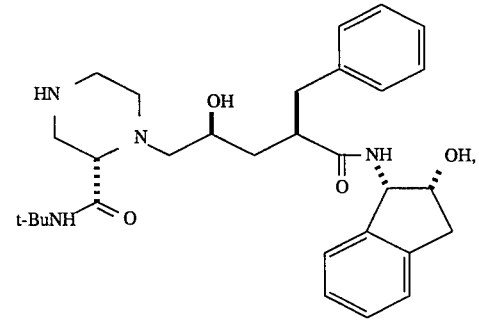

with between about one equivalent and about two equivalents of 3-pyridinecarboxaldehyde;

(b) adding a reducing agent selected from $NaBH(OAc)_3$ and formic acid, and maintaining for at least 5 minutes the resulting mixture at a temperature range between about 20° C. to about 60° C.;

(c) to provide compound J or hydrate thereof.

* * * * *